United States Patent [19]
Fibbe et al.

[11] Patent Number: 6,013,067
[45] Date of Patent: *Jan. 11, 2000

[54] METHODS FOR INCREASING HEMATOPOIETIC CELLS

[75] Inventors: Willem E. Fibbe, Lisse, Netherlands; Angelika Grossman, Seattle, Wash.

[73] Assignee: ZymoGenetics, Inc., Seattle, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/482,212

[22] Filed: Jun. 7, 1995

[51] Int. Cl.$^7$ .................................................. A61M 31/00
[52] U.S. Cl. ................................ 604/500; 604/4; 530/351
[58] Field of Search ................................ 604/4–6, 20, 49; 530/351

[56] References Cited

U.S. PATENT DOCUMENTS

| | | | |
|---|---|---|---|
| 4,894,440 | 1/1990 | Rosenberg | 530/351 |
| 4,946,437 | 8/1990 | Sredni et al. | 604/49 |
| 5,571,686 | 11/1996 | Rosenberg et al. | 435/29 |

FOREIGN PATENT DOCUMENTS

| | | |
|---|---|---|
| 92/21402 | 12/1992 | WIPO . |
| 95/28907 | 11/1995 | WIPO . |

OTHER PUBLICATIONS

Papayannopoulou et al., *Blood 84 (10 Suppl. 1)*: 324A, 1994.
Snyder et al., *Hematology 1994 Education Program American Society of Hematology*: 96–106, 1994.
Kaushansky et al., *Nature 369*: 568–571, 1994.
Lok et al., *Nature 369*: 565–567, 1994.
McDonald, *Experimental Hematology 16*: 201–205, 1988.
Kaushansky, Polyfunctionality of Hematopoietic Regulators: The Metcalf Forum. *Stem Cells 12*: 91–97, 1994.
de Sauvage et al., *Nature 369*: 533–538, 1994.
Sprugel et al., *Blood 84*: 242a, 1994.
Metcalf, *Nature 369*: 519–520, 1994.
Sheridan et al., *Lancet 339*: 640–644, 1992.

*Primary Examiner*—Corrine M. McDermott
*Assistant Examiner*—William Noggle
*Attorney, Agent, or Firm*—Susan E. Lingenfelter

[57] ABSTRACT

Methods for increasing hematopoietic cells, including platelets and erythrocytes, in patients receiving bone marrow or peripheral blood stem cell transplants are disclosed. The methods comprise administering to a donor an amount of thrombopoietin sufficient to stimulate proliferation of cells of the myeloid lineage, collecting cells from the donor, and administering the collected cells to a recipient patient. The recipient patient may be treated with additional thrombopoietin. The methods are useful within allogeneic and autologous transplantation procedures.

17 Claims, 3 Drawing Sheets

METHODS FOR INCREASING HEMATOPOIETIC CELLS

BACKGROUND OF THE INVENTION

Hematopoiesis is the process by which blood cells develop and differentiate from pluripotent stem cells in the bone marrow. This process involves a complex interplay of polypeptide growth factors (cytokines) acting via membrane-bound receptors on their target cells. Cytokine action results in cellular proliferation and differentiation, with a response to a particular cytokine often being lineage-specific and/or stage-specific. Development of a single cell type, such as a platelet, from a stem cell may require the coordinated action of a plurality of cytokines acting in the proper sequence.

It was hypothesized for many years that the production of platelets may be regulated by specific humoral factors. Early experiments had shown that plasma or urine of thrombocytopenic animals contains an activity that promotes megakaryocytic colony formation and increases the size of marrow megakaryocytes. This activity is referred to in the literature as "thrombopoietin" (recently reviewed by McDonald, *Exp. Hematol.* 16: 201–205, 1988 and McDonald, *Am. J. Ped. Hematol. Oncol.* 14: 8–21, 1992). The low concentration of this activity and the lack of suitable bioassays long hampered the purification and characterization of the protein. Thrombopoietin has now been produced using genetically engineered cultured cells. See, de Sauvage et al., *Nature* 369: 533–538, 1994; Lok et al., *Nature* 369: 565–568, 1994; Kaushansky et al., *Nature* 369: 568–571, 1994; and Bartley et al., *Cell* 77: 1117–1124, 1994.

Thrombopoietin has been shown to increase platelet numbers in normal (Lok et al., ibid.) and thrombocytopenic (Sprugel et al., *Blood* 84 (10 Suppl. 1): 242a, 1994) animals, and to stimulate production of erythrocytes (Kaushansky et al., *J. Clin. Invest.*, in press). In vitro, TPO enhances survival and proliferation of $CD34^+$ cells destined to become megakaryocytes (Papayannopoulou et al., *Blood* 84 (10 Suppl. 1): 324a, 1994).

Although the cloning and characterization of TPO now permits investigation of its clinical use in stimulating thrombopoiesis, thrombocytopenia and anemia remain as significant clinical problems, such as in connection with chemotherapy and radiation therapy of cancer patients. There remains a particular need for methods of stimulating platelet production in patients receiving bone marrow transplants and peripheral blood stem cell transplants, including autologous transplants. There also remains a need for stimulating erythrocyte production. The present invention provides therapeutic methods that address these needs, and provides other, related advantages.

SUMMARY OF THE INVENTION

The present invention provides methods for increasing hematopoietic cells in a recipient patient in need of such increase. The methods comprise the steps of (a) administering to a donor an amount of thrombopoietin (TPO) sufficient to stimulate proliferation of cells of the myeloid lineage in the donor; (b) collecting cells from the donor, wherein the cells are bone marrow cells or peripheral blood stem cells; and (c) administering the bone marrow cells or peripheral blood stem cells to a recipient patient. The donor and recipient may be different individuals or the same individual. Within one embodiment of the invention, the recipient patient has been treated with chemotherapy or radiation therapy. Within another embodiment, after or concurrently with administering the bone marrow cells or peripheral blood stem cells, an amount of TPO sufficient to enhance platelet recovery or erythrocyte recovery is administered to the recipient patient.

Within another aspect, the present invention provides methods of preparing cells for transplantation comprising administering to a donor an amount of TPO sufficient to stimulate proliferation of cells of the myeloid lineage in the donor, and collecting cells from the donor, wherein the cells are bone marrow cells or peripheral blood stem cells.

Within a third aspect, the present invention provides a method of stimulating platelet recovery or erythrocyte recovery in a patient receiving chemotherapy or radiation therapy comprising (a) administering to the patient an amount of TPO sufficient to stimulate proliferation of cells of the myeloid lineage in the patient; (b) collecting bone marrow cells or peripheral blood stem cells from the patient prior to chemotherapy or radiation therapy; and (c) returning the collected cells to the patient subsequent to chemotherapy or radiation therapy. Within one embodiment this method further comprises administering to the patient, after or concurrently with returning the collected cells, an amount of TPO sufficient to enhance platelet recovery or erythrocyte recovery.

These and other aspects of the invention will become evident upon reference to the following detailed description and the attached drawings.

DETAILED DESCRIPTION OF THE INVENTION

Figure 1:
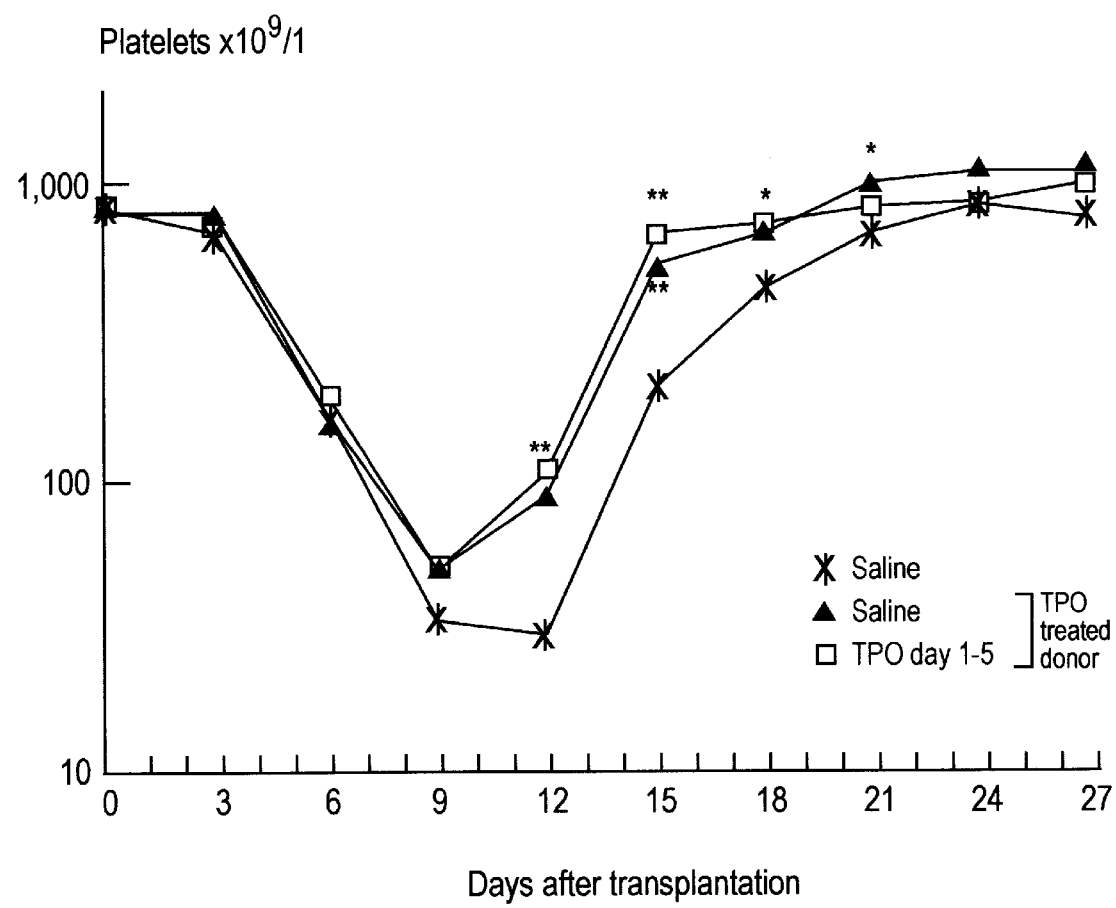
FIG. 1 illustrates the effect of transplantation of bone marrow cells from TPO- or vehicle-treated donor mice on platelet counts in recipient animals. In one experiment recipients of TPO-treated marrow were also treated with TPO (20 kU/day i.p.). Data are presented as means of 10–20 mice in two experiments. *, $p<0.05$; **, $p<0.01$.

The term "stem cell" is used herein to denote pluripotent hematopoietic stem cells and myeloid progenitor cells.

The term "transplantation" is used herein to denote the process of removing cells from a donor and subsequently administering the cells to a recipient. The term encompasses both allogeneic transplantation, wherein the donor and recipient are different individuals of the same species; and autologous transplantation, wherein the donor and recipient are the same individual.

The term "increasing hematopoietic cells" is used herein to denote the restoration or enhanced recovery of hematopoietic cell levels following their ablation, such as ablation resulting from disease or therapeutic intervention.

The term "thrombopoietin" encompasses proteins characterized by their ability to specifically bind to MPL receptor from the same species and to stimulate platelet production in vivo. In normal test animals, TPO is able to increase platelet levels by 100% or more within 10 days after beginning daily administration. A representative human TPO cDNA sequence is shown in SEQ ID NO: 1, and the corresponding amino acid sequence is shown in SEQ ID NO: 2. Analytical and experimental evidence indicates that the mature protein begins at residue Ser-22. Those skilled in the art will recognize that the illustrated sequences correspond to a single allele of the human TPO gene, and that allelic variation is expected to exist. Allelic variants include those containing silent mutations and those in which mutations result in amino acid sequence changes. It will also be evident that one skilled in the art could create additional variants, such as by engineering sites that would facilitate manipulation of the nucleotide sequence using alternative codons, by substitution of codons to produce conservative changes in amino acid sequence, etc. The use of allelic and engineered variant TPOs is contemplated by the present invention. In addition, amino-terminal TPO polypeptides of about 150 amino acids or more in length are known to be active (de Sauvage et al., ibid.; Bartley et al., ibid.; co-pending, commonly assigned U.S. patent application Ser. No. 08/346, 999), and the use of such truncated forms of TPO is within the scope of the present invention. Thrombopoietins from non-human species have been disclosed in the scientific literature (Lok et al., ibid.; de Sauvage et al., ibid; Bartley et al., ibid.).

The present invention provides methods for increasing hematopoietic cells in patients, particularly patients undergoing radiation therapy and/or chemotherapy, such as in the treatment of cancer. Such therapies kill dividing progenitor cells in the marrow and peripheral blood, limiting therapy and often requiring transfusions to restore circulating levels of platelets and other blood cells. Of particular interest are those patients receiving bone marrow and/or peripheral blood stem cell transplants following radiation therapy and patients suffering from congenital metabolic defects necessitating bone marrow transplant. Among these indications are bone marrow transplants associated with treatment of breast cancer, leukemia, lymphoma, multiple myeloma and congenital defects such as severe combined immune deficiency, thalassemia, and sickle cell anemia. Peripheral blood stem cell transplantation may be preferred in conditions where a risk of tumor cells in the blood is not present.

Methods for carrying out bone marrow and peripheral blood stem cell transplants are known in the art. For a review, see Snyder et al., "Transfusion Medicine" in Benz and McArthur, eds., *Hematology* 1994, American Society of Hematology, 96–106, 1994. Peripheral blood stem cells are collected by leukapheresis according to accepted clinical procedures. Hematopoietic progenitor cells can be selected on the basis of cell surface markers (e.g. CD34), allowing for enrichment of the desired cells and depletion of contaminating tumor cells. The collected cells are stored frozen in a suitable cryoprotectant (e.g. dimethyl sulfoxide, hydroxyethyl starch) until needed. Marrow cells are collected from donors by bone puncture under anesthesia. To reduce the volume, the collected marrow is usually processed to separate plasma from the cellular components. Removal of plasma can also eliminate red cell incompatibilities in allogeneic transplantation. The cell fraction can be enriched for mononuclear cells using density gradient techniques or automated separation methods and depleted of T cells using various cytotoxic agents. Collected marrow cells are cryopreserved according to established procedures that include controlled-rate freezing and the use of cryoprotectants. Stem cells are thawed in a warm water bath immediately prior to use to minimize loss associated with thawing. In the case of allogeneic transplants, donors and recipients are tissue matched to minimize the risk of graft-versus-host disease.

An increase in hematopoietic cells results from transplantation into a recipient patient of stem cells, particularly cells of the myeloid lineage, including $CD34^+$ stem cells and cells derived from $CD34^+$ stem cells. Of particular interest are cells in the megakaryocyte and erythrocyte lineages, which reconstitute the recipient's platelet and erythrocyte populations, respectively.

Within the present invention, a donor is treated, prior to donation of marrow or peripheral blood cells, with TPO in an amount sufficient to stimulate proliferation of cells of the myeloid lineage. Such an amount will generally be in the range of 0.5 μg/kg/day to 40 μg/kg/day, preferably 1 μg/kg/day to 20 μg/kg/day. Treatment of the donor will be carried out for a period of from one to several days, preferably about 2–5 days, during a period of from 3 days to 2 weeks prior to harvesting of bone marrow or peripheral blood stem cells. It is preferred to treat the donor during a period of five to ten days prior to harvesting of cells. The increase in $CD34^+$ stem cells and other cells of the myeloid lineage in the donor will be manifested by improved recovery of platelet and/or erythrocyte levels in the transplant recipient.

Within one embodiment of the invention, the recipient is treated with TPO after transplantation to further enhance platelet recovery. It has been found that post-transplantation treatment with TPO improves survival of lethally-irradiated test animals given bone marrow from TPO-treated donors. "An amount of thrombopoietin sufficient to enhance platelet recovery" is that amount that produces a statistically significant reduction in time for recovery of normal platelet levels or a statistically significant increase in platelet count as compared to untreated patients. Doses of TPO used in post-transplantation treatment will generally be in the range of 0.5 μg/kg/day to 40 μg/kg/day administered for from about 3 to about 20 days. In general, patients receiving bone marrow transplants will require longer post-transplantation treatment than those receiving peripheral blood stem cell transplants.

For use within the present invention, TPO can be prepared using genetically engineered, cultured cells according to methods generally known in the art. To summarize these methods, a DNA molecule encoding TPO is joined to other DNA sequences which provide for its maintenance and transcription in a host cell. The resulting expression vector is inserted into the host cell, and the resulting "transformed" or "transfected" cells are cultured in a suitable nutrient medium. Baby hamster kidney (BHK) cells are a preferred host. It is preferred to engineer the cells to secrete the TPO into the medium, although TPO can be recovered from cell lysates and processed in vitro to yield active protein. See, in general, de Sauvage et al., ibid.; Lok et al., ibid.; Kaushansky et al., *Nature* 369: 568–571, 1994; Wendling et al., *Nature* 369: 571–574, 1994; Bartley et al., ibid.; and co-pending, commonly assigned U.S. patent applications Ser. No. 08/366,859 and Ser. No. 08/347,029, which are incorporated herein by reference in their entirety.

TPO may be purified from cell-conditioned culture media by a combination of chromatographic and other techniques, including direct capture on a dye-ligand affinity matrix and ion-exchange chromatography. contaminating proteins may be removed by adsorption to hydroxyapatite.

For pharmaceutical use, TPO is formulated for parenteral, particularly intravenous or subcutaneous, delivery according to conventional methods. Intravenous administration will be by bolus injection or infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents (e.g. phosphate buffer), albumin or a non-ionic detergent to prevent protein loss on vial surfaces, etc. In addition, TPO may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences,* Gennaro, ed., Mack Publishing Co., Easton Pa., 1990, which is incorporated herein by reference.

The invention is further illustrated by the following, non-limiting examples.

EXAMPLES

Example 1

Mouse thrombopoietin was prepared using transfected baby hamster kidney cells (BHK 570 cells, ATCC CRL 10314). Serum-free medium contained 145 kU/ml of TPO activity, wherein 10 units are defined as the amount of TPO giving half-maximal stimulation in a mitogenesis ($^3$H-thymidine incorporation) assay using BaF3 cells transfected with an expression vector encoding the human MPL receptor (Vigon et al., *Proc. Natl. Acad. Sci. USA* 89: 5640–5644, 1992) as target cells. BaF3 is an interleukin-3 dependent pre-lymphoid cell line derived from murine bone marrow (Palacios and Steinmetz, Cell 41: 727–734, 1985; Mathey-Prevot et al., *Mol. Cell. Biol.* 6: 4133–4135, 1986). Cells were exposed to test samples in the presence of $^3$H-thymidine. The amount of $^3$H-thymidine incorporated into cellular DNA was quantitated by comparison to a standard curve of human TPO. Mouse TPO samples were effective in colony forming assays in a range of approximately 100–400 U/ml. In vivo activities were seen in the range of 20–40 kU/day in mice. For in vivo experiments, TPO was diluted to the desired concentration in endotoxin-free phosphate-buffered saline (PBS) and administered as intraperitoneal or subcutaneous injections.

Female Balb-C mice (age range 8–12 weeks) were obtained from Broekman B. V. (Someren, The Netherlands) and fed commercially available rodent chow and provided with acidified water ad libitum. Transplant recipients were maintained in a pathogen-free environment and provided with water containing ciprofloxacin at a concentration of 1 mg/ml, polymyxine-B at 70 µg/ml, and saccharose at 2 g/100 ml.

Recipient mice were placed in a polymethylmeta-acetate box and lethally (8.5 Gy) irradiated using a Philips SL 75-5/6 mV linear accelerator (Philips Medical Systems, Best, The Netherlands). Irradiation was divided in two parts in posterior-anterior and anterior-posterior position, at a dose rate of 4 Gy/minute. The mice were transplanted with $10^5$ bone marrow cells from steady-state donor mice. Transplantation was carried out within four hours of marrow harvesting. Groups of 5 recipient mice were treated with TPO at a dose of 20 kU/day intraperitoneally (i.p.) on days 1–5, 3–8 or 3–12 after transplantation. Control animals were transplanted with an equal amount of marrow cells and given saline at similar time intervals after transplantation. In comparison with saline-treated control recipients, TPO administration did not result in accelerated platelet reconstitution. A dose of 30 kU/day administered subcutaneously (s.c.) on days 1–14 was also ineffective in accelerating platelet recovery. No effects were seen on reconstitution of white blood cells or red blood cells.

In a second set of experiments, donor mice were treated with TPO for five consecutive days at a dose of 20 kU/day i.p. per mouse. At day 5 the mice were sacrificed, and blood, bone marrow and spleens were harvested. White blood cells, red blood cells and platelets were counted on a Sysmex 800 counter (TOA Medical Electronics Company, Kobe, Japan). TPO treatment induced a 2.5-fold increase in the numbers of platelets, but had no effect on the numbers of white blood cells or red blood cells.

Progenitor cell levels were also determined in the TPO-treated donor mice. Bone marrow cells were harvested by flushing femurs under sterile conditions with RPMI 1640 containing 500 µg/ml penicillin, 250 µg/ml streptomycin, and 2% fetal bovine serum (FBS) (GIBCO BRL, Gaithersburg, Md.). Single-cell suspensions of the spleens were prepared by mashing the organs and washing once with RPMI 1640 containing 2% FBS. To determine colony forming units, CFU-GM were cultured according to published procedures (Fibbe et al., *J. Immunol.* 148: 417, 1992). Briefly, bone marrow cells were cultured in microtiter plates containing $10^4$ cells/well in semi-solid medium in the presence of murine GM-CSF (1.25 ng/ml). Peripheral blood mononuclear cells and spleen cells were cultured in 3.5 cm dishes containing $5 \times 10^5$ cells/ml and $10^6$ cells/ml, respectively. Cells were cultured in a fully humidified atmosphere at 37° C. containing 5% $CO_2$. After 6 days of culture the number of colonies (defined as aggregates of >20 cells) were scored using an inverted microscope. The CFU-mix assay was performed in an identical fashion in 3.5 cm dishes in the presence of a combination of 1.25 ng/ml recombinant murine GM-CSF, 2 U/ml recombinant human EPO, 25 ng/ml recombinant murine IL-3, 5% transferrin, 5% bovine serum albumin, 5% $10^{-3}$ β-mercaptoethanol, and 7.5% Iscove's modified Dulbecco's medium (IMDM). After 6 to 7 days of culture at 37° C. in a fully humidified, 5% $CO_2$ atmosphere, the number of colony forming cells was scored using an inverted microscope. TPO treatment resulted in increased numbers of colony forming units (CFU) and BFU-Es in the bone marrow or spleen in comparison with saline-treated controls (Table).

TABLE

| | Donor Treatment | |
|---|---|---|
| | TPO | Saline |
| Femur | | |
| Nucleated cells (×$10^6$) | 18.4 ± 4.7 | 19.9 ± 4.3 |
| CFU (×$10^3$) | 55.3 ± 12.5* | 38.6 ± 5.2 |
| BFU-E (×$10^3$) | 24.0 ± 4.9 | 16.4 ± 2.3 |
| Spleen | | |
| Nucleated cells (×$10^6$) | 71.8 ± 35.0 | 78.4 ± 42.5 |
| CFU (×$10^3$) | 27.3 ± 16.9 | 16.3 ± 11.4 |
| BFU-E (×$10^3$) | 10.2 ± 2.3 | 1.9 ± 0.7 |

Results are expressed as absolute cell numbers (mean ± S.D., n = 7) per organ (femur or spleen).
CFU represents the total number of colonies cultured in the CFU-mix assay.
*p < 0.05.

Lethally-irradiated recipient animals were transplanted with $10^5$ bone marrow cells from donors that had been treated with TPO at a dose of 20 kU/day i.p. for five consecutive days, or from saline-treated control donors. Blood samples were taken after transplantation from individual recipients every 3 days by tail vein bleeding. No difference in visible bleeding tendency was observed between recipients of TPO-modified or unmodified bone marrow cells.

Cell counts were analyzed using the student's T tests. In the MANOVA analysis, groups were compared with respect to their course over time. The analysis was performed on the log values of the data. Values of <0.05 were considered statistically significant. Curves were compared using the MANOVA test. Results showed that the reconstitution of platelets in recipients of TPO-treated marrow was significantly altered in comparison to control animals transplanted with an equal number of bone marrow cells from saline-treated control donors (FIG. 1). In addition, platelet nadir counts were higher in animals receiving TPO-treated marrow than those receiving control marrow ($88 \times 10^9$ vs. $30 \times 10^9$ at day 12 after transplantation, mean of 20 mice). As shown in FIG. 1, post-transplant treatment with 20 kU/day TPO i.p. on days 1–5 did not result in a further acceleration of platelet reconstitution in mice that received marrow from TPO-treated donors.

Figure 2:
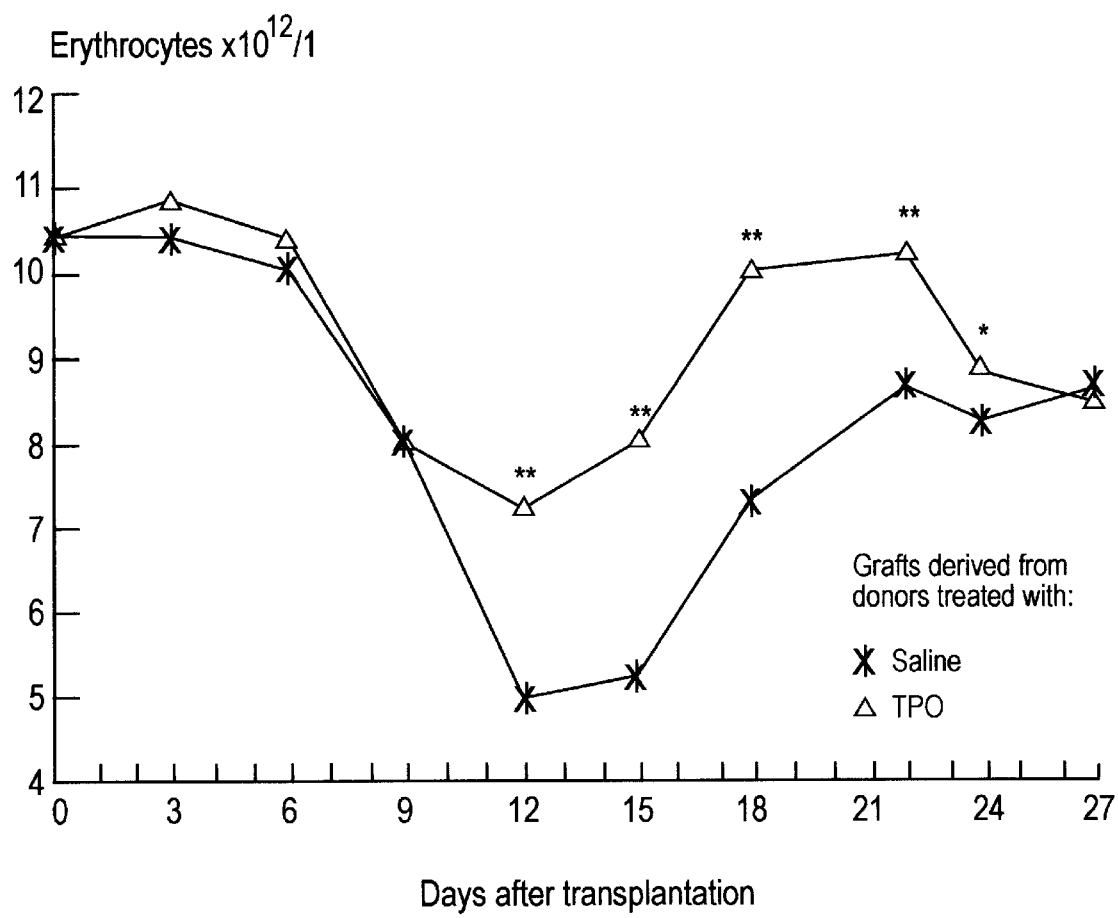
FIG. 2 illustrates the effect of transplantation of bone marrow cells from TPO- or vehicle-treated donor mice on erythrocyte counts in recipient animals. Data are expressed as mean of 20 mice in two experiments. *, $p<0.05$; **, $p<0.005$.

In addition to an accelerated reconstitution of platelets, recipients of TPO-modified bone marrow cells also exhibited accelerated reconstitution of erythrocytes (FIG. 2). The erythrocyte nadir counts were also significantly higher in these animals than in controls transplanted with an equal number of unmodified bone marrow cells. Experiments were performed to further substantiate that this effect was due to a direct activity of TPO on erythropoiesis and not related to differences in platelet counts and bleeding tendency. In this experiment recipient animals were not bled until 12 days after transplantation, at which time the recipient mice were sacrificed, and the numbers of bone marrow and blood-derived progenitor cells were assessed. Recipients of TPO-modified bone marrow cells had a higher number of BFU-E colonies/femur ($770\pm386$ vs $422\pm320$, mean$\pm$SD, n=5) and higher reticulocytes in the blood (44% vs. 8%, mean of 5 mice) than controls transplanted with an equal number of unmodified bone marrow cells, although these differences did not reach statistical significance. Post-transplant treatement with TPO did not result in further acceleration of erythrocyte reconstitution at the doses tested.

Example 2

A second experiment was carried out to compare platelet counts in lethally irradiated mice receiving marrow from TPO-treated or non-treated donors, and to determine the effect of post-transplantation TPO treatment of the recipient animals.

B6D2 F1 mice were obtained from Taconic (Germantown, N.Y.) and housed under specific pathogen-free conditions. The mice were housed five per cage and received acidified water and food ad libitum. Forty female mice were used as recipients, and five male mice were used as donors.

Recombinant human TPO was prepared using transfected BHK 570 cells. The major molecular species was a 70 kD band. The preparation had a specific activity of 5641 U/$\mu$g. The protein was made up in 29 mM potassium phosphate buffer, pH 6.0, containing 0.05% polysorbate 80 and 0.13 M NaCl and stored frozen in 20 kU aliquots. TPO and vehicle solutions were thawed directly before use and were injected into mice once daily, subcutaneously.

Two donor mice were each treated with 20 kU of TPO per day for four days, then sacrificed by cervical dislocation on the fifth day. Control donors were treated with vehicle only. Femora were taken out aseptically, and bone marrow was flushed out with Ham's F12 (Fred Hutchinson Cancer Research Center, Seattle, Wash.) containing 2% fetal bovine serum by inserting a 25 g. needle connected to a syringe. The cell suspension was flushed twice through an 18 g. needle, a 20 g. needle, and a 22 g. needle to produce a single-cell suspension. Nucleated cells were counted in a hemocytometer.

On day −2, recipient mice were exposed to 1200 cGy total body irradiation from a $^{137}$Cs source (Gammacell 40 Irradiator, Atomic Energy of Canada Radiochemical Company, Kanata, Canada). Bone marrow transplants were performed two to four hours after irradiation. Twenty mice received bone marrow ($1 \times 10^5$ cells) from TPO-treated donors, and twenty mice received $1 \times 10^5$ cells from vehicle-treated donors. Recipients were treated with TPO (20 kU/day) beginning on day 1 (2 days after transplantation) and continuing for 14 days.

Mice were bled from the retroorbital sinus under ether anesthesia. Fifty $\mu$l blood samples were collected in heparinized micropipettes (VWR Scientific, Seattle, Wash.) and dripped into microtainer tubes with EDTA (Becton Dickinson, San Jose, Calif.). Blood was also dripped onto glass slides, and smears were prepared. Blood was analyzed in a Cell Dyn 3500 hematology analyzer (Abbott, Santa Clara, Calif.). Hematocrit, RBC counts, WBC counts and platelet counts were determined.

Figure 3:
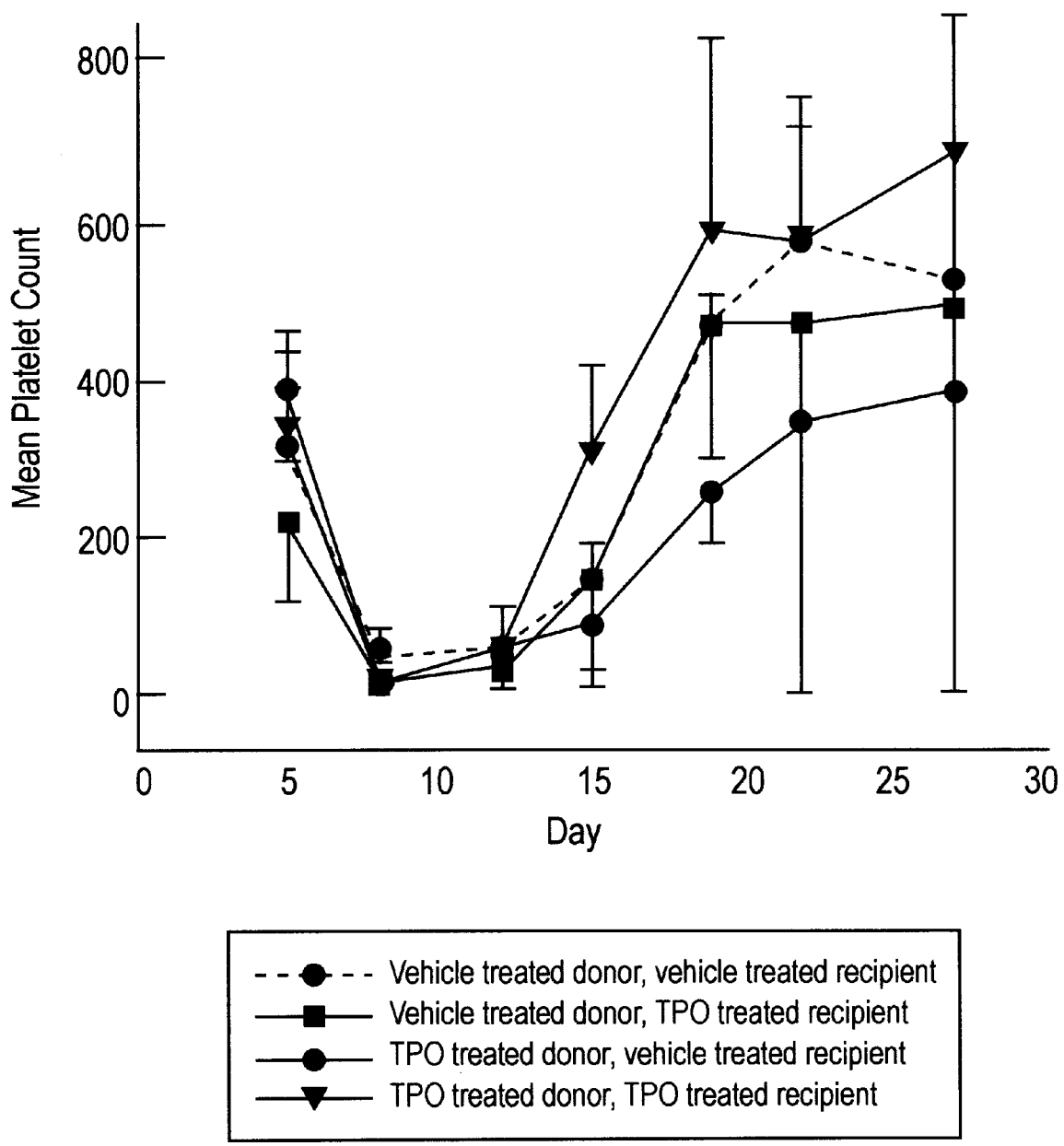
FIG. 3 illustrates platelet recovery in mice receiving marrow transplants from TPO- or vehicle-treated donors, with or without post-transplant TPO treatment.

In mice receiving marrow from control donors, platelet counts dropped on day 8 to low levels (below 6% of normal) and started to recover in TPO-treated and control animals on day 12 (FIG. 3). There was no difference between the two groups in platelet recovery. However, in the vehicle-treated controls only 3 of 10 animals survived, whereas in the TPO-treated group 7 of 9 animals survived. Death was related to hemorrhage. Standard deviations were large within the TPO-treated group because some animals with very low platelet counts were able to survive.

Mice receiving marrow from TPO-treated donors also had platelet numbers that were below 6% of normal on day 8. Animals that were treated with TPO for 14 days had, in general, a faster recovery in platelet counts. Eight of nine TPO-treated animals survived, whereas only four of nine vehicle-treated mice survived. RBCs recovered faster in mice that received TPO-pretreated bone marrow and were treated with TPO compared to controls. There was no influence of TPO treatment on white blood cell recovery.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for increasing platelets or erythrocytes in a recipient patient in need of such increase comprising:

administering to a donor an amount of thrombopoletin sufficient to stimulate MPL-dependent proliferation of cells of the myeloid lineage in the donor, wherein said thrombopoietin is a polypeptide of about 150 amino acids or more and is able to specifically bind MPL receptor from the same species;

collecting cells from the donor subsequent to the first administering step, wherein the collected cells are bone marrow cells or peripheral blood stem cells; and administering the collected bone marrow cells or peripheral blood stem cells to a recipient patient, whereby platelets or erythrocytes in the recipient patient are increased.

2. A method according to claim 1 wherein the recipient patient has been treated with chemotherapy or radiation therapy.

3. A method according to claim 1 wherein the donor and the recipient patient are the same individual.

4. A method according to claim 3 wherein the recipient patient is treated with chemotherapy or radiation between the collecting and second administering steps.

5. A method according to claim 1 wherein the cells are bone marrow cells.

6. A method according to claim 1 wherein the cells are peripheral blood stem cells.

7. A method according to claim 1 further comprising administering to the recipient patient, after or concurrently with administering the bone marrow cells or peripheral blood stem cells, an amount of thrombopoietin sufficient to enhance platelet recovery or erythrocyte recovery.

8. A method according to claim 1 wherein the thrombopoietin is human thrombopoietin.

9. A method of preparing cells for transplantation comprising:

administering to a donor an amount of thrombopoietin sufficient to stimulate MPL-dependent proliferation of cells of the myeloid lineage in the donor, wherein said thrombopoietin is a polypeptide of about 150 amino acids or more and is able to specifically bind MPL receptor from the same species; and collecting cells from the donor subsequent to the administering step, wherein the collected cells are bone marrow cells or peripheral blood stem cells.

10. A method according to claim 9 wherein the thrombopoietin is human thrombopoietin.

11. A method according to claim 9 wherein the cells are bone marrow cells.

12. A method according to claim 9 wherein the cells are peripheral blood stem cells.

13. A method of stimulating platelet or erythrocyte recovery in a patient receiving chemotherapy or radiation therapy comprising:

administering to the patient an amount of thrombopoietin sufficient to stimulate MPL-dependent proliferation of cells of the myeloid lineage in the patient, wherein said thrombopoietin is a polypeptide of about 150 amino acids or more and is able to specifically bind MPL receptor from the same species;

collecting bone marrow cells or peripheral blood stem cells from the patient subsequent to the first administering sten prior to chemotherapy or radiation therapy; and returning the collected cells to the patient subsequent to chemotherapy or radiation therapy, whereby platelet or erythrocyte recovery in the patient is stimulated.

14. A method according to claim 13 further comprising administering to the patient, after or concurrently with returning the collected cells, an amount of thrombopoietin sufficient to enhance platelet recovery or erythrocyte recovery.

15. A method according to claim 13 wherein the thrombopoietin is human thrombopoietin.

16. A method according to claim 13 wherein the cells are bone marrow cells.

17. A method according to claim 13 wherein the cells are peripheral blood stem cells.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1062 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..1059

(xi) SEQUENCE DESCRIPTION: SEQ ID NO:1:

```
ATG GAG CTG ACT GAA TTG CTC CTC GTG GTC ATG CTT CTC CTA ACT GCA      48
Met Glu Leu Thr Glu Leu Leu Leu Val Val Met Leu Leu Leu Thr Ala
 1               5                  10                  15

AGG CTA ACG CTG TCC AGC CCG GCT CCT CCT GCT TGT GAC CTC CGA GTC      96
Arg Leu Thr Leu Ser Ser Pro Ala Pro Pro Ala Cys Asp Leu Arg Val
             20                  25                  30

CTC AGT AAA CTG CTT CGT GAC TCC CAT GTC CTT CAC AGC AGA CTG AGC     144
Leu Ser Lys Leu Leu Arg Asp Ser His Val Leu His Ser Arg Leu Ser
         35                  40                  45

CAG TGC CCA GAG GTT CAC CCT TTG CCT ACA CCT GTC CTG CTG CCT GCT     192
Gln Cys Pro Glu Val His Pro Leu Pro Thr Pro Val Leu Leu Pro Ala
     50                  55                  60

GTG GAC TTT AGC TTG GGA GAA TGG AAA ACC CAG ATG GAG GAG ACC AAG     240
Val Asp Phe Ser Leu Gly Glu Trp Lys Thr Gln Met Glu Glu Thr Lys
 65                  70                  75                  80

GCA CAG GAC ATT CTG GGA GCA GTG ACC CTT CTG CTG GAG GGA GTG ATG     288
Ala Gln Asp Ile Leu Gly Ala Val Thr Leu Leu Leu Glu Gly Val Met
                 85                  90                  95

GCA GCA CGG GGA CAA CTG GGA CCC ACT TGC CTC TCA TCC CTC CTG GGG     336
Ala Ala Arg Gly Gln Leu Gly Pro Thr Cys Leu Ser Ser Leu Leu Gly
            100                 105                 110

CAG CTT TCT GGA CAG GTC CGT CTC CTC CTT GGG GCC CTG CAG AGC CTC     384
Gln Leu Ser Gly Gln Val Arg Leu Leu Leu Gly Ala Leu Gln Ser Leu
        115                 120                 125

CTT GGA ACC CAG CTT CCT CCA CAG GGC AGG ACC ACA GCT CAC AAG GAT     432
Leu Gly Thr Gln Leu Pro Pro Gln Gly Arg Thr Thr Ala His Lys Asp
    130                 135                 140

CCC AAT GCC ATC TTC CTG AGC TTC CAA CAC CTG CTC CGA GGA AAG GTG     480
Pro Asn Ala Ile Phe Leu Ser Phe Gln His Leu Leu Arg Gly Lys Val
145                 150                 155                 160

CGT TTC CTG ATG CTT GTA GGA GGG TCC ACC CTC TGC GTC AGG CGG GCC     528
Arg Phe Leu Met Leu Val Gly Gly Ser Thr Leu Cys Val Arg Arg Ala
                165                 170                 175

CCA CCC ACC ACA GCT GTC CCC AGC AGA ACC TCT CTA GTC CTC ACA CTG     576
Pro Pro Thr Thr Ala Val Pro Ser Arg Thr Ser Leu Val Leu Thr Leu
            180                 185                 190

AAC GAG CTC CCA AAC AGG ACT TCT GGA TTG TTG GAG ACA AAC TTC ACT     624
Asn Glu Leu Pro Asn Arg Thr Ser Gly Leu Leu Glu Thr Asn Phe Thr
        195                 200                 205

GCC TCA GCC AGA ACT ACT GGC TCT GGG CTT CTG AAG TGG CAG CAG GGA     672
Ala Ser Ala Arg Thr Thr Gly Ser Gly Leu Leu Lys Trp Gln Gln Gly
    210                 215                 220
```

```
TTC AGA GCC AAG ATT CCT GGT CTG CTG AAC CAA ACC TCC AGG TCC CTG      720
Phe Arg Ala Lys Ile Pro Gly Leu Leu Asn Gln Thr Ser Arg Ser Leu
225                 230                 235                 240

GAC CAA ATC CCC GGA TAC CTG AAC AGG ATA CAC GAA CTC TTG AAT GGA      768
Asp Gln Ile Pro Gly Tyr Leu Asn Arg Ile His Glu Leu Leu Asn Gly
                245                 250                 255

ACT CGT GGA CTC TTT CCT GGA CCC TCA CGC AGG ACC CTA GGA GCC CCG      816
Thr Arg Gly Leu Phe Pro Gly Pro Ser Arg Arg Thr Leu Gly Ala Pro
            260                 265                 270

GAC ATT TCC TCA GGA ACA TCA GAC ACA GGC TCC CTG CCA CCC AAC CTC      864
Asp Ile Ser Ser Gly Thr Ser Asp Thr Gly Ser Leu Pro Pro Asn Leu
        275                 280                 285

CAG CCT GGA TAT TCT CCT TCC CCA ACC CAT CCT CCT ACT GGA CAG TAT      912
Gln Pro Gly Tyr Ser Pro Ser Pro Thr His Pro Pro Thr Gly Gln Tyr
    290                 295                 300

ACG CTC TTC CCT CTT CCA CCC ACC TTG CCC ACC CCT GTG GTC CAG CTC      960
Thr Leu Phe Pro Leu Pro Pro Thr Leu Pro Thr Pro Val Val Gln Leu
305                 310                 315                 320

CAC CCC CTG CTT CCT GAC CCT TCT GCT CCA ACG CCC ACC CCT ACC AGC     1008
His Pro Leu Leu Pro Asp Pro Ser Ala Pro Thr Pro Thr Pro Thr Ser
                325                 330                 335

CCT CTT CTA AAC ACA TCC TAC ACC CAC TCC CAG AAT CTG TCT CAG GAA     1056
Pro Leu Leu Asn Thr Ser Tyr Thr His Ser Gln Asn Leu Ser Gln Glu
            340                 345                 350

GGG TAA                                                             1062
Gly
```

(2) INFORMATION FOR SEQ ID NO:2:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Leu Thr Glu Leu Leu Val Val Met Leu Leu Thr Ala
1               5                   10                  15

Arg Leu Thr Leu Ser Ser Pro Ala Pro Pro Ala Cys Asp Leu Arg Val
                20                  25                  30

Leu Ser Lys Leu Leu Arg Asp Ser His Val Leu His Ser Arg Leu Ser
            35                  40                  45

Gln Cys Pro Glu Val His Pro Leu Pro Thr Pro Val Leu Leu Pro Ala
        50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175
```

-continued

```
Pro Pro Thr Thr Ala Val Pro Ser Arg Thr Ser Leu Val Leu Thr Leu
            180             185             190

Asn Glu Leu Pro Asn Arg Thr Ser Gly Leu Leu Glu Thr Asn Phe Thr
        195             200             205

Ala Ser Ala Arg Thr Thr Gly Ser Gly Leu Leu Lys Trp Gln Gln Gly
    210             215             220

Phe Arg Ala Lys Ile Pro Gly Leu Leu Asn Gln Thr Ser Arg Ser Leu
225             230             235             240

Asp Gln Ile Pro Gly Tyr Leu Asn Arg Ile His Glu Leu Leu Asn Gly
            245             250             255

Thr Arg Gly Leu Phe Pro Gly Pro Ser Arg Arg Thr Leu Gly Ala Pro
            260             265             270

Asp Ile Ser Ser Gly Thr Ser Asp Thr Gly Ser Leu Pro Pro Asn Leu
        275             280             285

Gln Pro Gly Tyr Ser Pro Ser Pro Thr His Pro Pro Thr Gly Gln Tyr
        290             295             300

Thr Leu Phe Pro Leu Pro Pro Thr Leu Pro Thr Pro Val Val Gln Leu
305             310             315             320

His Pro Leu Leu Pro Asp Pro Ser Ala Pro Thr Pro Thr Pro Thr Ser
            325             330             335

Pro Leu Leu Asn Thr Ser Tyr Thr His Ser Gln Asn Leu Ser Gln Glu
            340             345             350

Gly
```